United States Patent
Chandrasekher et al.

(10) Patent No.: US 7,074,575 B2
(45) Date of Patent: Jul. 11, 2006

(54) USE OF INTERLEUKIN-19 TO TREAT OVARIAN CANCER

(75) Inventors: Yasmin A. Chandrasekher, Mercer Island, WA (US); Patricia A. McKernan, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 589 days.

(21) Appl. No.: 10/408,991

(22) Filed: Apr. 8, 2003

(65) Prior Publication Data

US 2003/0223958 A1 Dec. 4, 2003

Related U.S. Application Data

(60) Provisional application No. 60/372,344, filed on Apr. 11, 2002.

(51) Int. Cl.
  G01N 33/53 (2006.01)
  G01N 33/567 (2006.01)
(52) U.S. Cl. ............................. 435/7.2; 435/7.21
(58) Field of Classification Search ............. None
  See application file for complete search history.

(56) References Cited

U.S. PATENT DOCUMENTS

| 5,985,614 | A | 11/1999 | Rosen et al. | 435/69.52 |
| 6,583,270 | B1 | 6/2003 | Rosen et al. | 530/351 |
| 2002/0072089 | A1 | 6/2002 | Holtzman et al. | 435/69.1 |

FOREIGN PATENT DOCUMENTS

| WO | 03/086298 | 10/2003 |
| WO | 03/087307 | 10/2003 |
| WO | 04/024894 | 3/2004 |

OTHER PUBLICATIONS

Parish-Novak et al., "Interleukins 19, 20 and 24 Signal through Two Distinct Receptor Complexes," *J. Biol. Chem.* 277(49):47517-47523, 2002.

Gallagher et al., "Cloning, expression and initial characterisation of interleukin-19 (IL-19), a novel homologue of human interleukin-10 (IL-10)," *Genes and Immunity* 1:442-450, 2000.

Liao et al., "IL-19 Induces Production of IL-6 and TNF-α and Results in Cell Apoptosis Through TNF-α," *J. Immunol.* 4288-3310, 2002.

Ghoreschi et al., "Interleukin-4 therapy of psoriasis induces Th2 responses and improves human autoimmune disease," *Nature Medicine* 9(1):40-46, 2003.

Chang et al., "Crystal Structure of Interleukin-19 Defines a New Subfamily of Helical Cytokines," *J. Biol. Chem.* 278(5):3308-3313, 2003.

*Primary Examiner*—Prema Mertz
(74) *Attorney, Agent, or Firm*—Shelby J. Walker

(57) ABSTRACT

The present invention relates to the anti-cancer activity of IL-19 polypeptide molecules. IL-19 is a cytokine involved in inflammatory processes and human disease. The present invention includes Use of IL-19 for decreasing proliferation of ovarian cancer cells, treating ovarian cancer, amongst other uses disclosed. IL-19 polypeptides can be administered alone, or can be fused to cytotoxic moieties, and can be administered in conjunction with radiation or chemotherapeutic agents.

1 Claim, No Drawings

SEQUENCE LISTING

```
<160> NUMBER OF SEQ ID NOS: 2

<210> SEQ ID NO 1
<211> LENGTH: 985
<212> TYPE: DNA
<213> ORGANISM: Homo sapiens
<220> FEATURE:
<221> NAME/KEY: CDS
<222> LOCATION: (63)...(593)

<400> SEQUENCE: 1
gaattcggca cgaggactga gaggagacac aaggagcagc ccgcaagcac caagtgagag         60 gc atg aag tta cag tgt gtt tcc ctt tgg ctc ctg ggt aca ata ctg            107
   Met Lys Leu Gln Cys Val Ser Leu Trp Leu Leu Gly Thr Ile Leu
    1               5                  10                  15 ata ttg tgc tca gta gac aac cac ggt ctc agg aga tgt ctg att tcc           155
Ile Leu Cys Ser Val Asp Asn His Gly Leu Arg Arg Cys Leu Ile Ser
                     20                  25                  30 aca gac atg cac cat ata gaa gag agt ttc caa gaa atc aaa aga gcc           203
Thr Asp Met His His Ile Glu Glu Ser Phe Gln Glu Ile Lys Arg Ala
                 35                  40                  45 atc caa gct aag gac acc ttc cca aat gtc act atc ctg tcc aca ttg           251
Ile Gln Ala Lys Asp Thr Phe Pro Asn Val Thr Ile Leu Ser Thr Leu
             50                  55                  60 gag act ctg cag atc att aag ccc tta gat gtg tgc tgc gtg acc aag           299
Glu Thr Leu Gln Ile Ile Lys Pro Leu Asp Val Cys Cys Val Thr Lys
         65                  70                  75
```

-continued

```
aac ctc ctg gcg ttc tac gtg gac agg gtg ttc aag gat cat cag gag    347
Asn Leu Leu Ala Phe Tyr Val Asp Arg Val Phe Lys Asp His Gln Glu
 80                  85                  90                  95 cca aac ccc aaa atc ttg aga aaa atc agc agc att gcc aac tct ttc    395
Pro Asn Pro Lys Ile Leu Arg Lys Ile Ser Ser Ile Ala Asn Ser Phe
                100                 105                 110 ctc tac atg cag aaa act ctg cgg caa tgt cag gaa cag agg cag tgt    443
Leu Tyr Met Gln Lys Thr Leu Arg Gln Cys Gln Glu Gln Arg Gln Cys
            115                 120                 125 cac tgc agg cag gaa gcc acc aat gcc acc aga gtc atc cat gac aac    491
His Cys Arg Gln Glu Ala Thr Asn Ala Thr Arg Val Ile His Asp Asn
        130                 135                 140 tat gat cag ctg gag gtc cac gct gct gcc att aaa tcc ctg gga gag    539
Tyr Asp Gln Leu Glu Val His Ala Ala Ala Ile Lys Ser Leu Gly Glu
    145                 150                 155 ctc gac gtc ttt cta gcc tgg att aat aag aat cat gaa gta atg tcc    587
Leu Asp Val Phe Leu Ala Trp Ile Asn Lys Asn His Glu Val Met Ser
160                 165                 170                 175 tca gct tgatgacaag gaacctgtat agtgatccag ggatgaacac cccctgtgcg    643
Ser Ala gtttactgtg ggagacagcc caccttgaag gggaaggaga tggggaaggc cccttgcagc    703
tgaaagtccc actggctggc ctcaggctgt cttattccgc ttgaaaatag ccaaaaagtc    763
tactgtggta tttgtaataa actctatctg ctgaaaggc ctgcaggcca tcctgggagt    823
aaagggctgc cttcccatct aatttattgt gaagtcatat agtccatgtc tgtgatgtga    883
gccaagtgat atcctgtagt acacattgta ctgagtggtt tttctgaata aattccatat    943
tttacctatg aaaaaaaaaa aaaaaaaagc ggccgcctcg ag    985
```

<210> SEQ ID NO 2
<211> LENGTH: 177
<212> TYPE: PRT
<213> ORGANISM: Homo sapiens

<400> SEQUENCE: 2

```
Met Lys Leu Gln Cys Val Ser Leu Trp Leu Leu Gly Thr Ile Leu Ile
 1               5                  10                  15

Leu Cys Ser Val Asp Asn His Gly Leu Arg Arg Cys Leu Ile Ser Thr
                20                  25                  30

Asp Met His His Ile Glu Glu Ser Phe Gln Glu Ile Lys Arg Ala Ile
            35                  40                  45

Gln Ala Lys Asp Thr Phe Pro Asn Val Thr Ile Leu Ser Thr Leu Glu
     50                  55                  60

Thr Leu Gln Ile Ile Lys Pro Leu Asp Val Cys Cys Val Thr Lys Asn
 65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
        115                 120                 125

Cys Arg Gln Glu Ala Thr Asn Ala Thr Arg Val Ile His Asp Asn Tyr
    130                 135                 140
```

-continued

```
Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Ser Ser
                165                 170                 175

Ala
```

USE OF INTERLEUKIN-19 TO TREAT OVARIAN CANCER

REFERENCE TO RELATED APPLICATIONS

The present application is related to U.S. Provisional Application Ser. No. 60/372,344 filed Apr. 11, 2002. Under 35 U.S.C. § 119(e)(1), this application claims benefit of said Provisional Applications.

BACKGROUND OF THE INVENTION

Cancer of the ovary is the leading cause of death from gynecologic malignancies and the fourth common cause of cancer-related death among women. This is in spite of the fact that the occurrence of ovarian cancer is relatively rare. Only 1.5% of women develop the disease, and it is only the seventh most common cause of cancer in women.

Ovarian cancer can be divided into three sub-types depending on the cell type involved, namely, epithelial, stromal and germ cell tumors.

At least 80% of malignant ovarian tumors arise form the coelomic epithelium. The most common type is serous crystadenocarcinoma, which accounts for 75% of cases of epithelial ovarian cancer.

Most women (75%) present with advanced-stage disease, and most have vague, nonspecific symptoms, such as dyspepsia, bloating, early-satiety anorexia, gas pains and backache. The most common early finding is an adnexal mass, which is often solid, irregular, and fixed. A patient may be asymptomatic until the disease is advanced. Occasionally, a patient presents with severe abdominal pain secondary to torsion of the ovarian mass. Late in the course, pelvic pain, anemia, cachexia, and abdominal swelling due to ovarian enlargement or accumulation of ascitic fluid usually occur. Nodular implants noted on the rectovaginal examination suggest extensive pelvic malignant disease.

Stromal tumors constitute only a tenth of ovarian malignancies but account for most of the hormone-secreting tumors.

Germ cell tumors comprise less than 5 percent of ovarian malignancies, occur in young women, and have a higher incidence in African-American women than Caucasian women. Functional effects of germ cell or stromal tumors include hyperthyroidism, feminization, and virilization.

After surgery to remove the tumor chemotherapy is usually provided. The initial chemotherapeutic regimen is three to six courses of chemotherapy. Paclitaxel is combined with cisplatin or carboplatin. Other chemotherapeutic drugs include topotecan, hexamethylmelamine, ifosfamide, doxorubicin, bleomycin and etoposide. In spite of the regimens, the five-year survival rate of patients with stage II disease is only fifty to seventy percent and thirty to forty percent for patients with stage III disease.

Thus, there is a need for new therapeutics that can be used to treat ovarian cancer.

DESCRIPTION OF THE INVENTION

The present invention fills this need by administering interleukin-19 (IL-19) to a mammalian having ovarian cancer. The present invention also provides a method for inhibiting the growth of ovarian cancer cells by bringing IL-19 or fragments comprising helices A–D of IL-19, into contact with said cancerous ovarian cells. Interleukin-19, and fragments comprising helices A–D of IL-19, can be produced according to the method described in U.S. Pat. No. 5,985,614. The polynucleotide sequence of IL-19 is shown in SEQ ID NO:1 and corresponding amino acid sequence is shown in SEQ ID NO:2; the mature secreted form of the IL-19 polypeptide is shown from amino acid number 23 (His) to 177 (Ala) of SEQ ID NO:2.

The quantities of IL-19 for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 µg to 1000 µg per kilogram of body weight per day. However, the doses may be higher or lower as can be determined by a medical doctor with ordinary skill in the art. Excipients and stabilizers can possible be added. These include glycine, histidine, glutamate, aspartate, sugars, sucrose, trehalose, galactose sorbitol, arginine, D-and/or L amino acids, sugar alcohols, lactose, maltose, threonine, lysine, methionine, isoleucine, a surface active agent such as TWEEN 80, TWEEN 20, polyethylene glycol (PEG) (particularly those PEGs having molecular weights between 1000 and 35000 Da), cetyl alcohol, polyvinylpyrrolidone, polyvinyl alcohol, lanolin alcohol and sorbitan. A reducing agent may be included, such as cysteine, N-acetyl-cysteine, and thioglycerol. For a complete discussion of drug formulations and dosage ranges see *Remington's Pharmaceutical Sciences*, 18$^{th}$ Ed., (Mack Publishing Co., Easton, Pa., 1996), and *Goodman and Gilman's: The Pharmacological Bases of Therapeutics*, 9$^{th}$ Ed. (Pergamon Press 1996).

In addition, as IL-19 is useful in treating ovarian or cervical-specific cancers, the anti-tumor and anti-proliferative activity and effect of IL-19 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these-cell lines are capable of metastasis to the lung in C57BL6 mice. The Lewis lung carcinoma model has recently been used in mice to identify an inhibitor of angiogenesis (O'Reilly M S, et al. *Cell* 79: 315–328,1994). C57BL6/J mice are treated with an experimental agent either through daily injection of recombinant protein, agonist or antagonist or a one-time injection of recombinant adenovirus. Three days following this treatment, $10^5$ to $10^6$ cells are implanted under the dorsal skin. Alternatively, the cells themselves may be infected with recombinant adenovirus, such as one expressing IL-19, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., IL-19, on the ability of the tumor to recruit vasculature and undergo metastasis can thus be assessed. In addition, aside from using adenovirus, the implanted cells can be transiently transfected with IL-19. Use of stable IL-19 transfectants as well as use of induceable promoters to activate IL-19 expression in vivo are known in the art and can be used in this system to assess IL-19 induction of metastasis. Moreover, purified IL-19 or IL-19-conditioned media can be directly injected in to this mouse model, and hence be used in this system. For general reference see, O'Reilly M S, et al. *Cell* 79:315–328, 1994; and Rusciano D, et al. Murine Models of Liver Metastasis. *Invasion Metastasis* 14:349–361, 1995.

Similarly, animal tumor models such as human xenograft models in immunocompromised animals are used for cervical and ovarian cancer models and are known in the art. For example, one ovarian carcinoma model is as follows: NIH:OVCAR-5 cells injected into Swiss nude mice, as disclosed in Molpus, K L et al, *Int. J. Cancer* 68:588–95 (1996), which characterizes a xenograft model of human ovarian carcinoma which produces intraperitoneal carcinomatosis and metastases in mice. For example, one cervical carcinoma model is as follows: Cervical carcinoma: ME180 and SiHa human cervical squamous cell carcinoma lines grown in SCID mice. See, Moreno-Merlo F et al, *Br. J. Cancer* 81: 989–93 (1999) and Vukovic, V. et al, Int. J. *Radiat Oncol Biol Phys* 52:837–43 (2002).

Suitable detectable molecules may be directly or indirectly attached to the IL-19 polypeptide, and include radionuclides, enzymes, substrates, cofactors, inhibitors, fluorescent markers, chemiluminescent markers, magnetic particles and the like. Suitable cytotoxic molecules may be directly or indirectly attached to the polypeptide, and include bacterial or plant toxins (for instance, diphtheria, toxin, saporin, *Pseudomonas* exotoxin, ricin, abrin and the like), as well as therapeutic radionuclides, such as iodine-131, rhenium-188 or yttrium-90 (either directly attached to the polypeptide, or indirectly attached through means of a chelating moiety, for instance). Polypeptides may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide. For these purposes, biotin/streptavidin is an exemplary complementary/anticomplementary pair.

In addition, IL-19 polypeptide-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a cytokine (e.g., IL-19), a detectable molecule, a cytotoxic molecule or a complementary molecule to a cell or tissue type of interest, e.g., to ovarian or cervical tissue. In instances where the domain only fusion protein includes a complementary molecule, the anti-complementary molecule can be conjugated to a detectable or cytotoxic molecule. Such domain-complementary molecule fusion proteins thus represent a generic targeting carrier or vehicle for cell/tissue-specific delivery of generic anti-complementary-detectable/cytotoxic molecule conjugates.

In another embodiment, IL-19 cytokine fusion proteins can be used for in vivo killing of target tissues (for example, ovarian cancer, or cervical cancer, or leukemia, lymphoma, lung cancer, colon cancer, melanoma, pancreatic cancer, skin, blood and bone marrow cancers, or other cancers wherein IL-19 receptors are expressed) (See, generally, Chang, C. H. et al, *Mol Cancer Ther* 7:553–63(2002)). The described fusion proteins enable targeting of a cytokine to a desired site of action, thereby providing an elevated local concentration of cytokine. Suitable IL-19 polypeptides target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the IL-19 polypeptide targets tumor cells or cancerous tissues, such polypeptide may be conjugated with a radionuclide, and particularly with a beta-emitting radionuclide, to reduce restenosis (e.g., in vascular tissue). Such therapeutic approaches pose less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide described herein can be delivered intravenously, intraarterially or intraductally, or may be introduced locally at the intended site of action.

For pharmaceutical use, the IL-19 are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a protein in combination with a pharmaceutically acceptable vehicle, such as saline, buffered saline, 5% dextrose in water or the like. Formulations may further include one or more excipients, preservatives, solubilizers, buffering agents, albumin to provent protein loss on vial surfaces, etc. In addition, the IL-19 may be combined with other cytokines, particularly early-acting cytokines such as stem cell factor, IL-3, IL-6, IL-11 or GM-CSF. When utilizing such a combination therapy; the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of IL-19 is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The IL-19 can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5–15 lg/kg; IL-3, 1–5 lg/kg; and G-CSF, 1–25 lg/kg. Combination therapy with EPO, for example, is indicated in anemic patients with low EPO levels.

For pharmaceutical use, the IL-19 polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a IL-19 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of IL-19 is an amount sufficient to produce a clinically significant change in a cancer, cell growth or immune function.

The present invention also contemplates chemically modified IL-19 polypeptide is linked with a polymer. Illustrative IL-19 polypeptides are soluble polypeptides comprising a mature IL-19 polypeptide or a fragment of the IL-19 polypeptide comprising helices A–D of the polypeptide. Typically, the polymer is water soluble so that the IL-19 polypeptide conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1–C10) alkoxy, or aryloxy derivatives thereof (see, for example, Harris, et al., U.S. Pat. No. 5,252,714).

The polymer may be branched or unbranched. Moreover, a mixture of polymers can be used to produce IL-19 polypeptide conjugates.

IL-19 polypeptide conjugates used for therapy can comprise pharmaceutically acceptable water-soluble polymer moieties. Suitable water-soluble polymers include polyethylene glycol (PEG), monomethoxy-PEG, mono-(C1–C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide copolymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. An IL-19 polypeptide conjugate can also comprise a mixture of such water-soluble polymers.

One example of a IL-19 polypeptide conjugate comprises an IL-19 polypeptide moiety and a polyalkyl oxide moiety attached to the N-terminus of the IL-19 polypeptide moiety. PEG is one suitable polyalkyl oxide. As an illustration, IL-19 polypeptide can be modified with PEG, a process known as "PEGylation." PEGylation of IL-19 polypeptide can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, IL-19 polypeptide conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an IL-19 polypeptide. An example of an activated PEG ester is PEG esterified to N-hydroxysuccinimide. As used herein, the term "acylation" includes the following types of linkages between IL-19 polypeptide and a water soluble polymer: amide, carbamate, urethane, and the like. Methods for preparing PEGylated IL-19 polypeptide by acylation will typically comprise the steps of (a) reacting a IL-19 polypeptide with PEG (such as a reactive ester of an aldehyde derivative of PEG) under conditions whereby one or more PEG groups attach to IL-19 polypeptide, and (b) obtaining the reaction product(s). Generally, the optimal reaction conditions for acylation reactions will be determined based upon known parameters and desired results. For example, the larger the ratio of PEG:IL-19 polypeptide, the greater the percentage of polyPEGylated IL-19 polypeptide product.

The product of PEGylation by acylation is typically a polyPEGylated IL-19 polypeptide product, wherein the lysine ε-amino groups are PEGylated via an acyl linking group. An example of a connecting linkage is an amide. Typically, the resulting IL-19 polypeptide will be at least 95% mono-, di-, or tri-pegylated, although some species with higher degrees of PEGylation may be formed depending upon the reaction conditions. PEGylated species can be separated from unconjugated IL-19 polypeptides using standard purification methods, such as dialysis, ultrafiltration, ion exchange chromatography, affinity chromatography, and the like.

PEGylation by alkylation generally involves reacting a terminal aldehyde derivative of PEG with IL-19 polypeptide in the presence of a reducing agent. PEG groups can be attached to the polypeptide via a —CH$_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of IL-19 polypeptide monopolymer conjugates.

Reductive alkylation to produce a substantially homogenous population of monopolymer IL-19 polypeptide conjugate molecule can comprise the steps of: (a) reacting a IL-19 polypeptide with a reactive PEG under reductive alkylation conditions at a pH suitable to permit selective modification of the α-amino group at the amino terminus of the IL-19 polypeptide, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer IL-19 polypeptide conjugates, the reductive alkylation reaction conditions are those that permit the selective attachment of the water-soluble polymer moiety to the N-terminus of IL-19 polypeptide. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: IL-19 polypeptide need not be as large because more reactive groups are available. Typically, the pH will fall within the range of 3 to 9, or 3 to 6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to IL-19 polypeptide will generally be in the range of 1:1 to 100:1. Typically, the molar ratio of water-soluble polymer to IL-19 polypeptide will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharnacol. Ther.* 59:636 (1996), Monkarsh et al., *Anal. Biochem.* 247:434 (1997)). This method can be employed for making IL-19 polypeptide-comprising homodimeric, heterodimeric or multimeric soluble receptor conjugates.

A pharmaceutical composition comprising IL-19 polypeptides can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95–123 (CRC Press 1995); Bremer et al., "Protein Delivery with Infusion Pumps," in *Protein Delivery: Physical Systems*, Sanders and Hendren (eds.), pages 239–254 (Plenum Press 1997); Yewey et al., "Delivery of Proteins from a Controlled Release Injectable Implant," in *Protein Delivery: Physical Systems*, Sanders and Hendren (eds.), pages 93–117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3–24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

IL-19 polypeptides with IL-19 receptor binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51–93 (CRC Press 1995); Roskos and Maskiewicz, "Degradable Controlled Release Systems Useful for Protein Delivery," in *Protein Delivery: Physical Systems*, Sanders and Hendren (eds.), pages 45–92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified IL-19 polypeptides, for example IL-19 polypeptides linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

IL-19 can also me administered in conjunction with other treatments for ovarian cancer such as surgery and chemotherapy. Examples of chemotherapeutic agents include but are not limited to paclitaxel, cisplatin, carboplatin, topotecan, hexamethylmelamine, ifosfamide, doxorubicin, bleomycin, Taxol, and etoposide.

Within one aspect, the present invention provides a method for inhibiting the growth and or proliferation of ovarian cancer cells comprising bringing IL-19 polypeptide into contact with the ovarian cancer cells in an amount sufficient to inhibit or reduce the proliferation of the ovarian cancer cells.

Within a second aspect, the present invention provides a method for treating a female mammal afflicted with ovarian cancer comprising administering to the female an isolated IL-19 polypeptide an amount of a composition of IL-19 polypeptide sufficient to inhibit or reduce the proliferation of the ovarian cancer. In one embodiment, the method is as described above, wherein the IL-19 polypeptide is administered in conjunction with radiation. In another embodiment, the method is as described above, wherein the IL-19 polypeptide is administered in conjunction with a chemotherapeutic agent. In another embodiment, the method is as described above, wherein the chemotherapeutic agent is selected from the group consisting of paclitaxel, cisplatin, carboplatin, topotecan, hexamethylmelamine, ifosfamide, doxorubicin, bleomycin, Taxol, and etoposide.

Within a third aspect, the present invention provides a method for treating a female mammal afflicted with ovarian cancer comprising administering to the female an isolated IL-19 polypeptide an amount of a composition of IL-19 polypeptide sufficient to inhibit or reduce the proliferation of the ovarian cancer, and wherein the IL-19 polypeptide is fused with a cytotoxic moiety. In another embodiment, the method is as described above, wherein the cytotoxic moiety is a bacterial or plant toxin, cytotoxic radionuclide or cytotoxic drug.

Within another aspect, the present invention provides a method of reducing proliferation of ovarian cancer cells comprising administering to a mammal with a ovarian neoplasm an amount of a composition of IL-19 polypeptide sufficient to reduce proliferation of the neoplastic ovarian cells. In one embodiment, the method is as described above, wherein the IL-19 polypeptide is administered in conjunction with radiation. In another embodiment, the method is as described above, wherein the IL-19 polypeptide is administered in conjunction with a chemotherapeutic agent. In another embodiment, the method is as described above, wherein the chemotherapeutic agent is selected from the group consisting of paclitaxel, cisplatin, carboplatin, topotecan, hexamethylmelamine, ifosfamide, doxorubicin, bleomycin, Taxol, and etoposide. In another embodiment, the method is as described above, wherein the IL-19 polypeptide is fused with a cytotoxic moiety. In another embodiment, the method is as described above, wherein the cytotoxic moiety is a bacterial or plant toxin, cytotoxic radionuclide or cytotoxic drug.

The invention is further illustrated by the following non-limiting examples.

EXAMPLE

We tested IL-19 in an Ovcar3 (ATCC #HTB-161) cytoxicity assay to measure the ability of IL-19 to prevent cells from growing during normal growth conditions. We used MTT reagent (Promega, Madison, USA) as our detection and readout for this cell inhibition assay. Procedure of a cytoxicity assay: Ovcar3 Cytotoxicity Assay Ovcar3 (ATCC #HTB-161) cells were plated at a density of 5000 cells/100 ul/well in clear 96 well TC plates. Cells were plated in complete growth media consisting of RPMI containing 20% FBS, 0.01 mg/ml insulin, 2% HEPES, 1% Sodium Pyruvate and 1% Glutamax. Cells were incubated overnight at 37° C. in a 5% CO2 incubator.

The following day, media was removed from the cells and replaced with 100 ul/well of appropriately diluted samples. All sample dilutions were done in complete growth media. Samples were incubated on the cells for 72 hours.

After incubation, an MTT assay was done on the cells using the manufacturer's protocol (Promega #PAG4100). Dye solution was incubated on the cells 4 hours, followed by a 1 hour incubation with the stop solution. Absorbance was then read on the Victor II and percent inhibition was calculated from the wells containing complete growth media only.

RESULTS

Retnoic Acid gave a 29% inhibition of growth at 3 uM, 34% at 10 uM, 43% at 31 uM, and 83% at 100 uM (positive control)

IL-19 gave a 4% inhibition of growth at 1 ng/ml, 9% at 10 ng/ml, 23% at 100 ng/ml and 52% at 1000 ng/ml.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting the growth and proliferation of ovarian cancer cells in vitro comprising contacting the ovarian cancer cells with an IL-9 polypeptide of amino acid secquence set forth in SEQ ID NO:2 with the ovarian cancer cells in an amount sufficient to inhibit the growth and proliferation of the ovarian cancer cells.

* * * * *

UNITED STATES PATENT AND TRADEMARK OFFICE
CERTIFICATE OF CORRECTION

PATENT NO. : 7,074,575 B2  
APPLICATION NO. : 10/408991  
DATED : July 11, 2006  
INVENTOR(S) : Yasmin A. Chandrasekher and Patricia A. McKernan It is certified that error appears in the above-identified patent and that said Letters Patent is hereby corrected as shown below:

TITLE page, ITEM (57) Abstract, at line 4, replace "Use" with -- use --.

Claim 1, at line 3, replace "IL-9" with -- IL-19 --.

Signed and Sealed this

Twenty-eighth Day of November, 2006

JON W. DUDAS  
*Director of the United States Patent and Trademark Office*